United States Patent [19]

Shepherd

[11] 4,117,158

[45] Sep. 26, 1978

[54] 4-(MONOALKYLAMINO)BENZONITRILES USEFUL AS ANTI-ATHEROSCLEROTIC AGENTS

[75] Inventor: Robert Gordon Shepherd, South Nyack, N.Y.

[73] Assignee: American Cyanamid Company, Stamford, Conn.

[21] Appl. No.: 836,946

[22] Filed: Sep. 27, 1977

[51] Int. Cl.$^2$ .................. A61K 31/275; C07C 121/78
[52] U.S. Cl. ............................... 424/304; 260/308 D; 260/465 D; 260/465 E; 424/199; 424/269
[58] Field of Search ..................... 260/465 E; 424/304

[56] References Cited

U.S. PATENT DOCUMENTS 3,868,416  2/1975  Albright et al. ................. 260/518 R

*Primary Examiner*—Dolph H. Torrence
*Attorney, Agent, or Firm*—Edward A. Conroy, Jr.

[57] ABSTRACT

This disclosure describes novel 4-(monoalkylamino)-benzonitriles and 5-[4-(monoalkylamino)phenyl]tetrazoles and homologs thereof useful as hypolipidemic and anti-atherosclerotic agents.

14 Claims, No Drawings

4-(MONOALKYLAMINO)BENZONITRILES USEFUL AS ANTI-ATHEROSCLEROTIC AGENTS

BRIEF SUMMARY OF THE INVENTION

This invention relates to new organic compounds; 4-(monoalkylamino)benzonitriles, 5-[4-(monoalkylamino)phenyl]-tetrazoles, homologs, derivatives and salts thereof; which may be represented by the following structural formula:

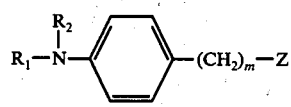

wherein $R_1$ is a straight chain or branched alkyl group of the formula $C_nH_{2n+1}$ wherein $n$ is an integer from 8 to 19, inclusive; $R_2$ is hydrogen or a group convertible in vivo thereinto such as methyl, ethyl, carboxylmethyl, lower alkanoyl ($C_1$-$C_6$), succinyl, 1-(sodium sulfo)lower alkyl, 1-(sodium sulfo)polyhydroxyalkyl or 1,3-bis(-sodium sulfo)-aralkyl; $m$ is 0, 1 or 2 with the proviso that when Z is cyano then $m$ may not be zero; and Z is selected from the group consisting of cyano and 5-tetrazolyl.

A preferred embodiment of this invention consists of those compounds in which $n$ is an integer from 14 to 19, inclusive, and R is hydrogen; either in the free or derivatized state, namely those of the structural formula:

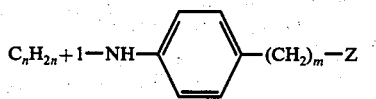

wherein $n$ is 14–19, and $m$ and $z$ are as hereinabove defined.

A more preferred embodiment of this invention consists of those compounds in which $n$ is an integer from 14 to 19, inclusive, and $R_2$ is hydrogen; either in the free or derivatized state, namely those of the structural formula:

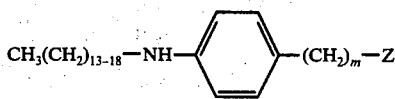

wherein $m$ and Z are as defined hereinabove.

The straight chain or normal alkyl groups for the substituent R may be, for example, octyl, nonyl, decyl, undecyl, dodecyl, tridecyl, tetradecyl, pentadecyl, hexadecyl, heptadecyl, octadecyl and nonadecyl. Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyl-tridecyl, 2,4,6,8-tetramethylnonyl, 1,4-dimethyl-1-ethylhexyl, 15-methylhexadecyl, 13,13-dimethyltetradecyl, 15,15-dimethylhexadecyl, and the like.

The invention also pertains to novel compositions of matter useful as anti-atherosclerotic agents and to methods of meliorating atherosclerosis by counteracting hyperlipemia and arterial plaque formation in mammals therewith; the active ingredients of said compositions of matter being the novel benzonitriles and phenyltetrazoles and homologs of the present invention thereof in the underivatized form or in the form of a pharmaceutically acceptable salt with an inorganic or organic acid. The invention also contemplates a method for lowering serum lipids and for meliorating atherosclerosis in mammals by the administration of said nitriles and tetrazoles.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,144. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

U.S. Pat. No. 3,868,416 discloses and claims certain 4-monoalkylaminobenzoic acid esters, pharmaceutically acceptable salts thereof, pharmaceutical compositions therewith and a method of lowering serum lipid levels in mammals therewith. No prior art is known which discloses 4-(monoalkylamino)benzonitriles or 5-[4-(monoalkylamino)phenyl]-tetrazoles and derivatives and salts thereof of this invention and no hypolipidemic activity has been reported in the literature for these compounds, and they are different in structure from other hypolipidemic agents. The compounds of this invention lower serum-lipid concentrations and also minimize atheroma formation in the aorta. These 4-(monoalkylamino)nitriles and tetrazoles provide the oral administration required of hypolipidemic agents, which patients usually take for many years. The anti-atherogenic activity of the alkylaminobenzoic acids mentioned above have been announced; Abstract No. 27, American Oil Chemists Society, 67th Meeting, New Orleans, April 21-24, 1976; Federation Proceedings 36, Abstract No. 4706 (1977).

We have now found that members of this class of compounds can safely and effectively lower both serum sterols and triglycerides in warm-blooded animals. Such actions on serum lipid components are considered to be very useful in the treatment of atherosclerosis, especially in contrast to available drugs whose action is much more limited. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The 4-(monoalkylamino)benzonitriles, 5-[4-(monoalkylamino)phenyl]tetrazoles, and homologs thereof of the present invention are, in general, crystalline solids having characteristic melting points and spectral characteristics. They are soluble in organic solvents such as lower alkanols, chloroform, benzene, dimethylformamide, and the like, but are generally insoluble in water. Also, the novel nitriles of the present invention are useful as intermediates for the preparation of the novel tetrazoles of the present invention.

The novel compounds of the present invention form non-toxic acid-addition salts with a variety of pharmacologically acceptable inorganic salt-forming reagents. Thus, acid-addition salts, formed by admixture of the organic free base with one or more equivalents of an acid, suitably in a neutral solvent, are formed with such acids as sulfuric, phosphoric hydrochloric, hydrobromic, and the like. The acid-addition salts of the present invention are, in general, crystalline solids, relatively soluble in water, methanol and ethanol but relatively insoluble in non-polar organic solvents such as diethyl ether, benzene, toluene, and the like. In addition, the tetrazole ring can form cationic salts with bases such as the alkali metal hydroxides.

The free nitriles and tetrazoles of this invention may be prepared generally as follows. p-Aminobenzonitrile in an organic solvent such as hexamethylphosphoramide is heated with an alkyl ($C_{8-19}$) bromide at a temperature of 80°-130° C. for 8-24 hours, cooling the mixture, adding water, and isolating the product therefrom. The nitriles may be purified by recrystallization from a solvent pair such as ether-hexanes. The acetonitriles are prepared accordingly by employing p-aminophenylacetonitrile at 50°-80° C.; similarly, the $\beta$-propionitriles from $\beta$-(aminophenyl)propionitrile. These alkylaminonitriles are also prepared by alkylations employing other alkyl halides, sulfates, tosylates or mesylates with or without solvent at 50°-150° C., using an equivalent of an organic or inorganic base instead of an excess of the aminonitrile as base. Alkylation of the alkali metal salts of 4-acylaminobenzonitriles is done similarly. Alternative methods of preparation are by reductive alkylation of amino nitriles with suitable carbonylalkanes and by diborane reduction of alkanoylaminonitriles or of chloroimides formed therefrom. Amination of 4-fluorobenzonitrile in hot excess alkylamine as solvent or of 4-bromobenzonitrile and lithium diisopropylamide in cold excess alkylamine are additional synthetic procedures. The nitrile group may be generated from aldehydes or their derivatives by conversion to oximes and treatment with trifluoroacetic anhydride, followed by alkaline removal of the N-trifluoroacetyl group. The alkylaminonitriles may be similarly prepared from N-alkanoyl derivatives with alkali and from N-protected intermediates such as N-t-butyloxycarbonyl derivatives with acid. The nitrile group in the acetonitriles and $\beta$-propionitriles may be synthesized from alkylamino (benzoyl and $\beta$-phenylethyl) halides, etc. and alkali cyanides in polar solvents at 40°-120° C. employing N-protecting groups when desired.

The 5-[p-alkyl($C_{8-19}$)aminophenyl]tetrazoles are prepared by treating a p-alkyl($C_{8-19}$)aminobenzonitrile with sodium azide and ammonium chloride in an organic solvent such as dimethylformamide at a temperature of 100°-140° C. for 24-28 hours, and then isolating the product therefrom after the addition of water. The 5-[p-alkyl($C_{8-19}$)aminobenzyl]-tetrazoles may be prepared accordingly by employing a p-alkyl($C_{8-19}$)aminophenylacetonitrile; and, $\beta$-[p-alkyl($C_{8-19}$)-aminophenyl]propionitriles are converted into the 5-$\beta$-[p-alkyl($C_{8-19}$)aminophenyl]ethyltetrazoles. Acetylation of monoalkylaminonitriles in pyridine with acetylating agents such as acetic anhydride, acetyl chloride and the like at 20° to 40° C. for 1-24 hours provide the N-acetyl derivatives after the addition of water. The acid-addition salts of the monoalkylaminonitriles may be conveniently prepared by treatment of the nitrile in a solvent such as diethyl ether, tetrahydrofuran, dimethoxyethane, and the like, with hydrogen chloride, hydrogen bromide and the like at room-temperature for a period of 3-30 minutes, and separating the acid-addition salt therefrom.

Certain derivatives

of the aminophenyl nitrogen atom are useful for providing greater solubility, more uniform and reliable intestinal absorption, and for a certain degree of modification of the pharmacology of the compounds of the present invention. Some of these derivatives can be converted to the corresponding N—H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)-alkyl derivatives are obtained by reaction of the benzonitriles or phenyltetrazoles, or suitable intermediates in certain cases, with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon of cinnamaldehyde itself.

The novel compounds of the present invention are not only hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 grams to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: A binder such as gum tragacanth, acacia,, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1 p-Hexadecylaminobenzonitrile p-Aminobenzonitrile (11.8 g., 0.1 mole) and 1-bromohexadecane (15.25 g., 0.05 mole) are dissolved in hexamethylphosphoramide (200 ml.) and heated under nitrogen in an oil-bath maintained at 120° for 22 hours. The reaction mixture is cooled to room temperature and water (50 ml.) is added gradually. The mixture is then chilled in an ice-bath. The precipitate is filtered, washed thoroughly with water and dried. It is then washed repeatedly with hexane and dried; 14.2 g. pale brownish yellow granular solid is obtained as homogeneous product. Crystallization from ether-hexane affords pale yellow prisms, melting point 63°-64° C.

In the above procedure replacement of 1-bromohexadecane with a bromoalkane ($C_{8-19}$) provides the following products:
p-octylaminobenzonitrile,
p-nonylaminobenzonitrile,
p-decylaminobenzonitrile,
p-undecylaminobenzonitrile,
p-(1-methylundecyl)aminobenzonitrile,
p-dodecylaminobenzonitrile,
p-tridecylaminobenzonitrile,
p-tetradecylaminobenzonitrile,
p-pentadecylaminobenzonitrile,
p-(14-methylpentadecyl)aminobenzonitrile,
p-heptadecylaminobenzonitrile,
p-octadecylaminobenzonitrile, and
p-nonadecylaminobenzonitrile.

The bromoalkanes include 1-bromo-14-methylpentadecane prepared as follows:

A solution of 3-methylbutylmagnesium bromide is prepared by treating 15.1 g. of 3-methylbutyl bromide with 2.7 g. of magnesium turnings in 50 ml. of dry tetrahydrofuran. The resultant Grignard reagent is added dropwise to a solution of 34.5 g. of 1,11-dibromoundecane and 0.2 g. of lithium copper chloride in 75 ml. of tetrahydrofuran. After 1 hour stirring at −10° C., the solution is evaporated, and the resultant oil is distilled in vacuo to yield the colorless 1-bromo-14-methylpentadecane.

EXAMPLE 2

5-(p-Hexadecylaminophenyl)tetrazole

Sodium azide (0.98 g., 0.015 mole) and $NH_4Cl$ are added to a solution of p-hexadecylaminobenzonitrile (5.13 g., 0.015 mole) in dimethylformamide. The mixture is stirred and heated in an oil bath maintained at 120° C. for 42 hours. The reaction mixture is cooled and then poured into ice-water with vigorous stirring. The precipitate separated is filtered, washed thoroughly with water and dried. The dry precipitate is washed repeatedly with ether and dried; 1.7 g. of a pale brown powder is obtained as a homogeneous product, melting point 114°–116° C. (decomp.).

In the above procedure replacement of p-hexadecylaminobenzonitrile with the p-alkyl($C_{8-19}$)aminobenzonitrile described in Example 1 provide the following products:
5-(p-octylaminophenyl)tetrazole,
5-(p-nonylaminophenyl)tetrazole,
5-(p-decylaminophenyl)tetrazole,
5-(p-undecylaminophenyl)tetrazole,
5-[p-(1-methylundecyl)aminophenyl]tetrazole,
5-(p-dodecylaminophenyl)tetrazole,
5-(p-tridecylaminophenyl)tetrazole,
5-(p-tetradecylaminophenyl)tetrazole,
5-(p-pentadecylaminophenyl)tetrazole,
5-[p-(14-methylpentadecyl)aminophenyl]tetrazole,
5-(p-heptadecylaminophenyl)tetrazole,
5-(p-octadecylaminophenyl)tetrazole, and
5-(p-nonadecylaminophenyl)tetrazole.

EXAMPLE 3 p-Hexadecylaminophenylacetonitrile

Following the procedure of Example 1 employing p-aminophenylacetonitrile at 60°–80° C. provides the product of the Example.

EXAMPLE 4 p-Alkyl($C_{8-19}$)aminophenylacetonitrile

Following the procedure of Example 1 employing a bromoalkane ($C_{8-19}$) with p-aminophenylacetonitrile at 60°–80° C. provide the product of the Example.

EXAMPLE 5

β-(p-Hexadecylaminophenyl)propionitrile

Following the procedure of Example 1 employing β-(p-aminophenyl)propionitrile at 60°–80° C. provides the product of the Example.

EXAMPLE 6

β-(p-Alkyl($C_{8-19}$)aminophenyl)propionitrile

Following the procedure of Example 1 employing a bromoalkane ($C_{8-19}$) with β-(p-aminophenyl)propionitrile at 60°–80° C. provide the product of the Example.

EXAMPLE 7

5-(p-Hexadecylaminobenzyl)tetrazole

Following the procedure of Example 2 employing p-hexadecylaminophenylacetonitrile provides the product of the Example.

EXAMPLE 8

5-(p-Alkyl($C_{8-19}$)aminobenzyl)tetrazole

Following the procedure of Example 2 p-alkyl($C_{8-19}$)aminophenylacetonitrile provide the product of the Example.

EXAMPLE 9

5-[β-(p-Hexadecylaminophenyl)ethyl]tetrazole

Following the procedure of Example 2 employing β-(p-hexadecylaminophenyl)propionitrile provides the product of the Example.

EXAMPLE 10

5-[β-(p-Alkyl($C_{8-19}$)aminophenyl)ethyl]tetrazole

Following the procedure of Example 2 employing β-(p-alkyl($C_{8-19}$)aminophenyl)propionitrile provides the product of the Example.

EXAMPLE 11

N-Acetyl p-Hexadecylaminobenzonitrile p-Hexadecylaminobenzonitrile (150 mg.) in pyridine (1 ml.) is treated with acetic anhydride (0.5 ml.), and the mixture is allowed to stand at room temperature for 3 hours. It is then poured into water, and the product of the Example is collected.

EXAMPLE 12 p-Hexadecylaminobenzonitrile Hydrochloride

Hydrogen chloride is bubbled with stirring into a solution of p-hexadecylaminobenzonitrile (1.0 g.) in anhydrous diethyl ether (50 ml.). Immediately a white precipitate forms, and after several minutes the product of the Examples is collected and washed with diethyl ether.

EXAMPLE 13

| Preparation of 50 mg. Tablets | | |
|---|---|---|
| Per Tablet | | Per 10,000 Tablets |
| 0.050 gm. | Active ingredient | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | | 15 gm. |
| 0.150 gm. | | 1490 gm. |

The active ingredient, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 14

| Preparation of Oral Suspension | |
|---|---|
| Ingredient | Amount |
| Active ingredient | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water   qs   ad | 100 ml. |

The sorbitol solution is added to 40 ml. of distilled water and the active ingredient is suspended therein. The saccharin, sodium benzoate, flavor and dye are added and dissolved. The volume is adjusted to 100 ml. with distilled water. Each ml. of syrup contains 5 mg. of active ingredient.

I claim:
1. A compound of the structural formula:

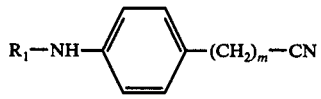

wherein $R_1$ is a straight chain or branched alkyl group of the formula $C_nH_{2n+1}$ wherein $n$ is an integer from 8 to 19, inclusive, and $m$ is 1 or 2; and the pharmacologically acceptable acid-addition salts thereof.

2. The compounds of claim 1 in the form of pharmaceutically acceptable acid-addition salts.

3. A compound of the structural formula:

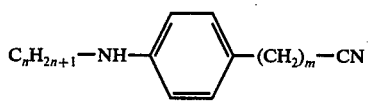

wherein $n$ is an integer from 14 to 19, inclusive, and $m$ is 1 or 2; and the pharmacologically acceptable acid-addition salts thereof.

4. A compound of the structural formula:

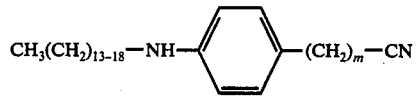

wherein $m$ is 1 or 2 and the pharmacologically acceptable acid-addition salth thereof.

5. p-(14-Methylpentadecyl)aminobenzonitrile.
6. p-Hexadecylaminobenzonitrile.
7. p-Hexadecylaminophenylacetonitrile.
8. β-(p-Hexadecylaminophenyl)propionitrile.
9. p-Hexadecylaminobenzonitrile hydrochloride.

10. The method of inhibiting atherosclerotic lesion development in a mammal comprising administering to said mammal an effective lesion development inhibiting amount of a compound of the formula:

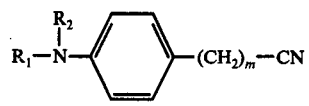

wherein $R_1$ is a straight chain or branched alkyl group of the formula $C_nH_{2n+1}$ wherein $n$ is an integer from 8 to 19, inclusive; $R_2$ is hydrogen, alkyl having up to 3 carbon atoms, 1-(sodium sulfo)alkyl or alkanoyl having up to 6 carbon atoms; $m$ is 0, 1 or 2; and the pharmaceutically acceptable acid-addition salts thereof.

11. The method of claim 10 wherein said compound is administered to provide a daily dosage of from about one mg. to about 250 mg. per kilogram of body weight of said mammal.

12. An anti-atherosclerotic composition in dosage unit form useful for preventing or diminishing atherosclerotic lesion formation in mammals comprising from about one mg. to about 250 mg. per kilogram of body weight per daily dosage unit of a compound of the formula:

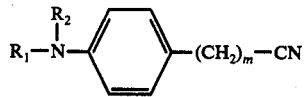

wherein $R_1$ is a straight chain or branched alkyl group of the formula $C_nH_{2n+1}$ wherein $n$ is an integer from 8 to 19, inclusive; $R_2$ is hydrogen, alkyl having up to 3 carbon atoms, 1-(sodium sulfo)alkyl or alkanoyl having up to 6 carbon atoms; $m$ is 0, 1 or 2, and the pharmaceutically acceptable acid-addition salts thereof; in association with a pharmaceutical carrier.

13. The method of inducing regression of atherosclerotic lesion development in a mammal comprising administering to said mammal an effective lesion regressive amount of a compound of the formula:

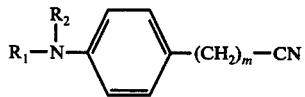

wherein $R_1$ is a straight chain or branched alkyl group of the formula $C_nH_{2n+1}$ wherein $n$ is an integer from 8 to 19, inclusive; $R_2$ is hydrogen, alkyl having up to 3 carbon atoms, 1-(sodium sulfo)alkyl or alkanoyl having up to 6 carbon atoms; $m$ is 0, 1 or 2; and the pharmaceutically acceptable acid-addition salts thereof.

14. The method of claim 13 wherein said compound is administered to provide a daily dosage of from about one mg. to about 250 mg. per kilogram of body weight of said mammal.

* * * * *